(12) United States Patent
Dang et al.

(10) Patent No.: US 9,848,805 B2
(45) Date of Patent: Dec. 26, 2017

(54) BIOSTABLE GLUCOSE PERMEABLE POLYMER

(71) Applicant: Medtronic MiniMed, Inc., Northridge, CA (US)

(72) Inventors: Tri T. Dang, Winnetka, CA (US); Henrik Egesborg, Hellerup (DK); Jakob Janting, Kogens Lyngby (DK); Rajiv Shah, Rancho Palos Verdes, CA (US); Daniel Aaskov, Gentofte (DK); Joseph F. Hall, Burbank, CA (US); Soren Aasmul, Holte (DK)

(73) Assignee: Medtronic MiniMed, Inc., Northridge, CA (US)

( * ) Notice: Subject to any disclaimer, the term of this patent is extended or adjusted under 35 U.S.C. 154(b) by 184 days.

(21) Appl. No.: 14/974,250

(22) Filed: Dec. 18, 2015

(65) Prior Publication Data

US 2017/0172471 A1   Jun. 22, 2017

(51) Int. Cl.

| | |
|---|---|
| A61B 5/145 | (2006.01) |
| A61B 5/1459 | (2006.01) |
| C08G 71/02 | (2006.01) |
| G01N 33/66 | (2006.01) |
| C08L 75/00 | (2006.01) |
| A61B 5/1473 | (2006.01) |
| C12Q 1/00 | (2006.01) |
| A61B 90/30 | (2016.01) |
| G01N 33/543 | (2006.01) |
| C12Q 1/54 | (2006.01) |

(52) U.S. Cl.
CPC ........ *A61B 5/14532* (2013.01); *A61B 5/1459* (2013.01); *A61B 5/14735* (2013.01); *C08G 71/02* (2013.01); *C08L 75/00* (2013.01); *G01N 33/66* (2013.01); *A61B 2090/306* (2016.02); *A61B 2562/12* (2013.01); *A61M 2230/201* (2013.01); *C12Q 1/006* (2013.01); *C12Q 1/54* (2013.01); *G01N 33/54393* (2013.01)

(58) Field of Classification Search
CPC .......... A61B 2090/306; A61B 2562/12; A61B 5/14532; A61B 5/1459; A61B 5/14735; C08G 71/02; A61M 2230/201; C12Q 1/006; C12Q 1/54; C08L 75/00; G01N 33/54393; G01N 33/66

See application file for complete search history.

(56) References Cited

U.S. PATENT DOCUMENTS

| | | | |
|---|---|---|---|
| 4,755,173 | A | 7/1988 | Konopka et al. |
| 5,391,250 | A | 2/1995 | Cheney, II et al. |
| 5,485,408 | A | 1/1996 | Blomquist |

(Continued)

*Primary Examiner* — Jennifer Wecker
(74) *Attorney, Agent, or Firm* — Gates & Cooper LLP

(57) ABSTRACT

A new biostable glucose permeable polymer has been developed which is useful, for example, in implantable glucose sensors. This biostable glucose permeable polymer has a number of advantageous characteristics and, for example, does not undergo hydrolytic cleavage and degradation, thereby providing a composition that facilitates long term sensor stability in vivo. The versatile characteristics of this polymer allow it to be used in a variety of contexts, for example to form the body of an implantable glucose sensor. The invention includes the polymer composition, sensor systems formed from this polymer composition, and methods for making and using such sensor systems.

20 Claims, 10 Drawing Sheets

(56) References Cited

U.S. PATENT DOCUMENTS

| | | | |
|---|---|---|---|
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 2007/0123819 A1 | 5/2007 | Mernoe et al. | |
| 2010/0160861 A1 | 6/2010 | Causey, III et al. | |
| 2011/0152654 A1* | 6/2011 | Wang | G01N 33/5438 600/347 |
| 2016/0249840 A1* | 9/2016 | Pesantez | A61B 5/14865 205/778 |

* cited by examiner

FIG. 1B

| | mol % | Size (Da) | Final Size (Da) |
|---|---|---|---|
| PEG Segment | 5 - 45 | 500 - 2000 | 10,000 - 400,000 |
| PPG Segment | 5 - 45 | 500 - 2000 | |
| NCO Linker | 20 - 80 | N/A | |
| Plasticizer | 10 - 60 | N/A | |

BIOSTABLE GLUCOSE PERMEABLE POLYMER

TECHNICAL FIELD OF THE INVENTION

This invention relates generally to polymeric materials and to methods of making and using such materials. The polymeric materials are hydrophilic, biocompatible, and suitable for use in biosensors, such as glucose sensors.

BACKGROUND OF THE INVENTION

Biosensors use biological recognition properties for selective detection of various analytes or biomolecules. Typically, the sensor will produce a signal that is quantitatively related to the concentration of the analyte. To achieve a quantitative signal, a recognition molecule or combination of molecules is often used to convert a biological recognition event into a quantitative response.

The need for the continuous in vivo monitoring of biological markers (analytes) in medicine has sparked a tremendous interest in the study of biosensors in recent years. Regardless of the type of biosensor, such devices and systems typically possess certain properties to function in vivo and provide an adequate signal. For example, elements of the biosensor should be compatible with the tissue to which it is attached, and be adequately safe such that allergic or toxic effects are not exerted. Further, the sensor should not readily degrade while in use in vivo. Finally, the sensor should accurately measure the analyte in the presence of proteins, electrolytes and medications, which may have the potential to interfere.

Without question, the greatest interest has been geared toward the development of sensors to detect glucose. There are several reasons for the wide-ranging interest in glucose sensors. In the healthcare arena, enzymatic glucose test strips are useful for monitoring the blood sugar of patients with diabetes mellitus. A sensor that has the ability to continuously monitor the blood, or interstitial glucose of a person with diabetes could provide great insight into the level of control that they have over their disease and avoid the need for repeated blood draws. Additionally, a continuously monitoring glucose sensor is one of the critical components necessary for the development of an artificial pancreas.

There is a need for a glucose sensor formed from biocompatible yet non-biodegradable polymeric components that offers physical and biological stability and strength, processibility, and the ability to be synthesized and manufactured in reasonable quantities and at reasonable prices. The present invention fulfills these needs and provides other related advantages.

SUMMARY OF THE INVENTION

As discussed in detail below, a new biostable glucose permeable polymer has been developed which is useful, for example, in implantable glucose sensors. This biostable glucose permeable polymer has a number of advantageous characteristics and, for example, does not undergo hydrolytic cleavage and degradation in vivo, thereby providing a composition that facilitates long term sensor stability in vivo. The versatile characteristics of this polymer allow it to be used in a variety of contexts, for example to form the body of an implantable glucose sensor.

The invention disclosed herein has a number of embodiments. One embodiment is glucose sensing system comprising a tubular housing having a first end and a second end, wherein the tubular housing comprises a biostable glucose permeable polymer disclosed herein. Typically this polymer is formed by combining an isocyanate, a polypropylene glycol-block-polyethylene glycol-block-polypropylene glycol having an average molecular weight ($M_r$) of from about 600 to about 1200 Daltons and a terephthalate, and formed so that the polymeric composition has a glucose permeability of at least $1 \times 10^{-8}$ cm$^2$/s at 37° C. in phosphate buffered saline. In some embodiments of the invention, the polymeric composition is biostable, exhibiting a less than a 5% weight loss after 7 days of implantation in vivo. In some embodiments of the invention, in a stress strain test, after 45° C. for 7 days, a tubular fiber of the polymeric composition can exhibit a tensile strength such that at a stress of 10 MpA and a strain of 200% (or 300%), the fiber does not fracture (see, e.g. FIG. 4).

In typical working embodiments of the glucose sensing system disclosed herein, the first end of the tubular housing is coupled to an optical fiber so as to form a seal with the first end; and/or the second end of the tubular housing is coupled to a membrane or a cap, thereby forming an internal reservoir within the tubular housing. In certain embodiments, the tubular housing is coupled to the optical fiber and/or the cap or membrane by solvent bonding so as to form a composition having certain structural features. For example using solvent bonding so that polymers in the polymeric composition and polymers in the optical fiber or polymers in the membrane/cap are entangled and attracted together by Van der Waals forces. Compositions designed in this way allow, for example, glucose to readily diffuse through interfaces between interfaces between the tubular housing and the cap, membrane of the like.

In illustrative embodiments of the invention, the tubular housing comprise an internal reservoir containing a glucose sensing complex comprising at least one glucose binding agent and at least one fluorophore. Typically in these embodiments, the components of the glucose sensing complex are lyophilized. In certain embodiments, the internal reservoir can comprise a hydrogel. In embodiments of the invention, the tubular housing is between 80 microns and 300 microns in diameter. In some embodiments of the invention, an internal reservoir is disposed on a side of the tubular housing. In some embodiments of the invention, an internal reservoir is disposed on a terminal end the tubular housing. In illustrative embodiments of the invention, the glucose sensing systems can comprise a processor, wherein the processor performs the steps of assessing optical signal data generated by the glucose sensing complex and transmitted by the optical fiber; and then computing a glucose concentration based upon the optical signal data.

Another embodiment of the invention is method for making a biostable glucose permeable polymer by combining together an isocyanate, a polypropylene glycol-block-polyethylene glycol-block-polypropylene glycol having an average molecular weight ($M_r$) of from about 600 to about 1200 Daltons; and a terephthalate. Optionally the biostable glucose permeable polymers have an average molecular weight of between 10,000 and 1,000,000. Daltons. In this method, the components are combined under conditions which produce a polymeric composition having a glucose permeability of at least $1 \times 10^{-8}$ cm$^2$/s at 37° C. in phosphate buffered saline. Typically these methods further comprise using an extrusion process to mold the polymeric composition, for example into a tubular form having a first end and a second end. Typically, the composition is manipulated to for a tubular structure between 80 microns and 300 microns in diameter. Certain methods of the invention include operatively coupling the first end of the tubular housing to an optical fiber so as to form a seal with the first end. These methods can include operatively coupling the second end of the tubular housing to a membrane or a cap so as to form a seal with the second end and an internal reservoir within the tubular housing. Optionally, the methods can comprise disposing a hydrogel in the internal reservoir.

In certain embodiments of the invention, cap or membrane (e.g. one formed from the biostable glucose permeable polymer composition) is coupled to the second end of a tubular housing using a solvent to dissolve the polymeric composition in the cap and/or membrane and the housing material in order to create adhesion between the cap and the second end of the tubular housing (e.g. so that polymers in the polymeric composition and polymers in the optical fiber or polymers in the membrane or cap are entangled and attracted together by Van der Waals forces). In certain embodiments, a cap or membrane is coupled to the tubular housing using a solvent vapor. In embodiments of the invention, the method can comprise disposing a glucose sensing complex within the internal reservoir. Optionally the glucose sensing complex is lyophilized. In embodiments of the invention, the method can comprise disposing a hydrogel within the internal reservoir.

Yet another embodiment of the invention is a hydrophilic polyurea composition formed by combining an isocyanate, a polypropylene glycol-block-polyethylene glycol-block-polypropylene glycol having an average molecular weight ($M_r$) of from about 600 to about 1200 Daltons, and a terephthalate. In this embodiment, the hydrophilic polyurea composition has a glucose permeability of at least $1 \times 10^{-8}$ $cm^2/s$ at 37° C. in phosphate buffered saline and is biostable, optionally such that the tubular housing has less than a 10% weight loss after 7 days of implantation in vivo. Typically, the hydrophilic polyurea composition comprises polymers have an average molecular weight of between 10,000 and 1,000,000. Daltons.

The invention additionally provides methods of measuring an analyte in a tissue of a subject using a implantable biosensor formed from the biostable glucose permeable polymer compositions disclosed herein. The method comprises introducing an implantable biosensor of the invention into the tissue of the subject, and detecting the signal generated by a transducer such as a glucose sensing complex that generates an optical signal in the presence of analyte. The amount of signal corresponds to the amount of analyte. Typically, the analyte is glucose and the transducer comprises a fluorophore.

BRIEF DESCRIPTION OF THE DRAWING

In FIG. 1A, L=1-5, M=4-14, N=1-5, P=2-25, R=1-750, S=5-450 and TO=4-2400. FIG. 1B is a table showing components of a non-biodegradable polymer embodiment of the invention. A variety of linkers and/or plasticizers can be used in embodiments of the invention. Compounds having aromatic, stiffer, and reaction specific NCO's can be selected to yield higher strength polymers. We also control the PEG/PPG segments and Plasticizers to fine tune the polymer's glucose permeability while maintaining sufficient physical strength. Individual sizes of the PEG/PPG can be used for controlling the degree of entanglement, having a tighter or looser polymer network. A variety of bi-functional phthalates can also be used in embodiments of the invention.

FIG. 5B shows how membranes have been coupled optical fibers and capped to form an assay compartment/reservoir.

DETAILED DESCRIPTION

All scientific and technical terms used in this application have meanings commonly used in the art unless otherwise specified.

Analyte (e.g. glucose) sensors designed for use in vivo use should be formed from elements selected to exhibit material characteristics that optimize that sensor performance. As discussed in detail below, a new biostable glucose permeable polymer has been developed which is useful, for example, in implantable glucose sensors. This biostable glucose permeable polymer has a number of advantageous characteristics and, for example, does not undergo hydrolytic cleavage and degradation, thereby providing a composition that facilitates long term sensor stability in vivo. The versatile characteristics of this polymer allow it to be used in a variety of contexts, for example to form sensors having both a material composition and three dimensional architecture suitable for implantable glucose sensors. Unless otherwise indicated, data on working examples disclosed herein was obtained from e-beam sterilized samples/articles.

The invention disclosed herein has a number of embodiments. One embodiment is glucose sensing system comprising a tubular housing having a first end and a second end, wherein the tubular housing comprises a biostable glucose permeable polymer disclosed herein. Typically this polymer is formed by combining an isocyanate, a polypropylene glycol-block-polyethylene glycol-block-polypropylene glycol having an average molecular weight ($M_r$) of from about 600 to about 1200 Daltons and a terephthalate, and formed so that the polymeric composition has a glucose permeability of at least $1 \times 10^{-8}$ $cm^2/s$ at 37° C. in phosphate buffered saline. In embodiments of the invention, the polymeric composition is biostable and has less than a 5% weight loss after 7 days of implantation in vivo.

Figure 1A:
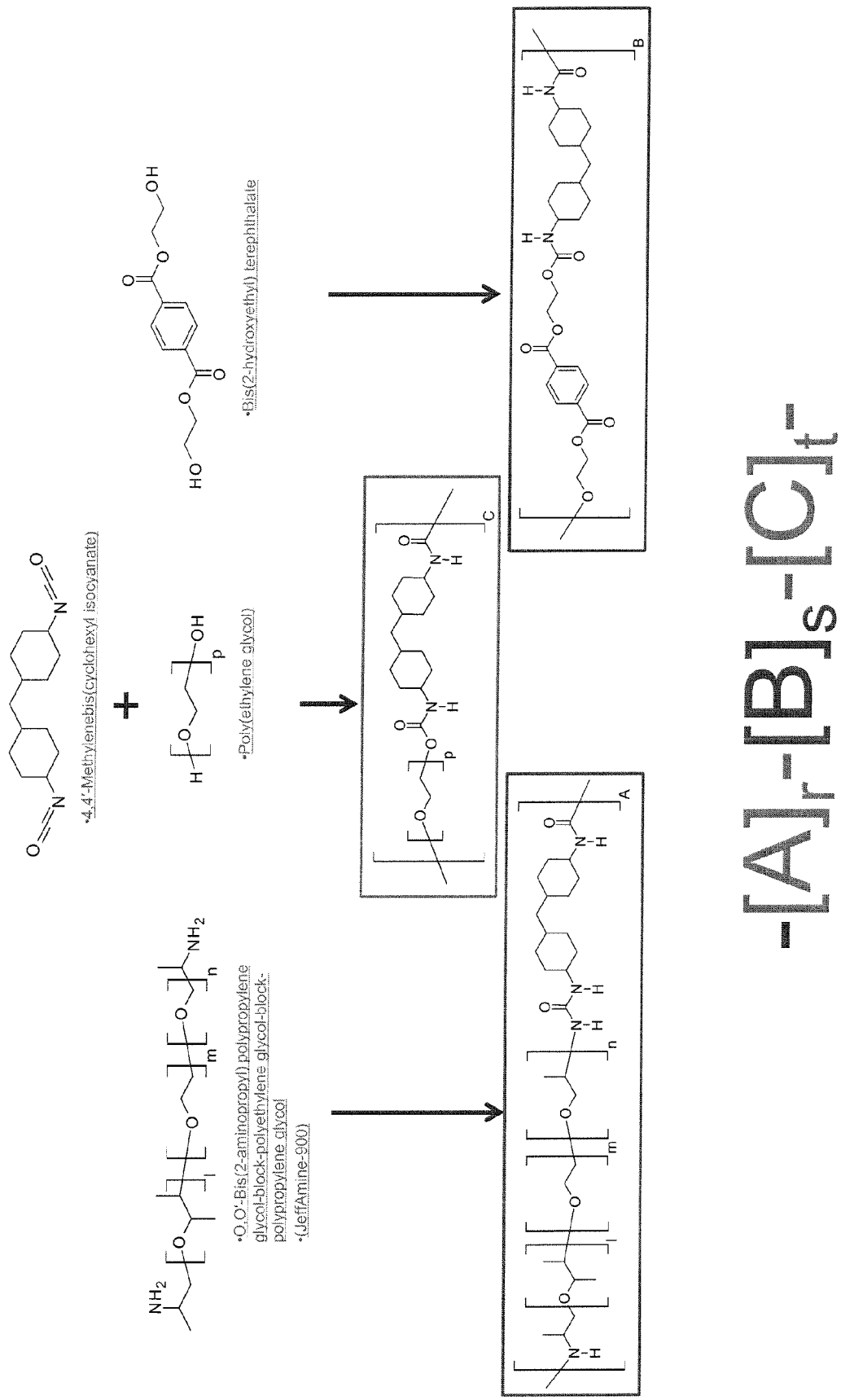
FIG. 1A is a schematic illustration of a non-biodegradable polymer embodiment of the invention.

FIG. 1A is a schematic illustration of a non-biodegradable polymer embodiment of the invention. In FIG. 1A, L=1-5, M=4-14, N=1-5, P=2-25, R=1-750, S=5-450 and TO=4-2400. FIG. 1B is a table showing components useful for forming a non-biodegradable polymer embodiment of the invention. Illustrative isocyanate compounds useful in making embodiments of the invention include for example:

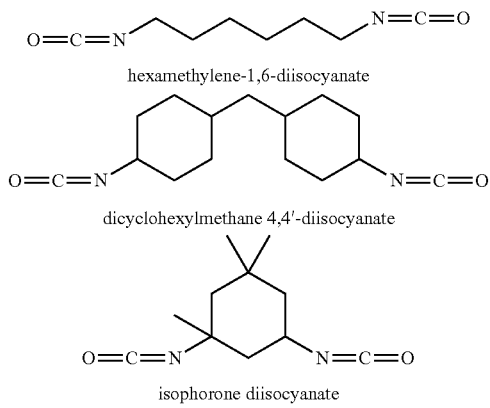

Illustrative terephthalate compounds useful in embodiments of the invention include for example bifunctional terephthalate comprising —OH moieties.

In typical working embodiments of the glucose sensing system disclosed herein, the first end of the tubular housing is coupled to an optical fiber so as to form a seal with the first end; and/or the second end of the tubular housing is coupled to a membrane or a cap, thereby forming an internal reservoir within the tubular housing. In certain embodiments, the tubular housing is coupled to the optical fiber and/or the cap or membrane by solvent bonding so as to form a composition having certain structural features. For example using solvent bonding so that polymers in the polymeric composition and polymers in the optical fiber or polymers in the membrane/cap are entangled and attracted together by Van der Waals forces. Compositions designed in this way allow, for example, glucose to readily diffuse through interfaces between the tubular housing and the cap, membrane of the like. This overcomes problems that can occur when adhesive materials compromise the ability of glucose to diffuse through bonded sensor components (e.g. when the material properties of an adhesive composition make it difficult for analytes such as glucose to diffuse therethrough).

Figure 2:
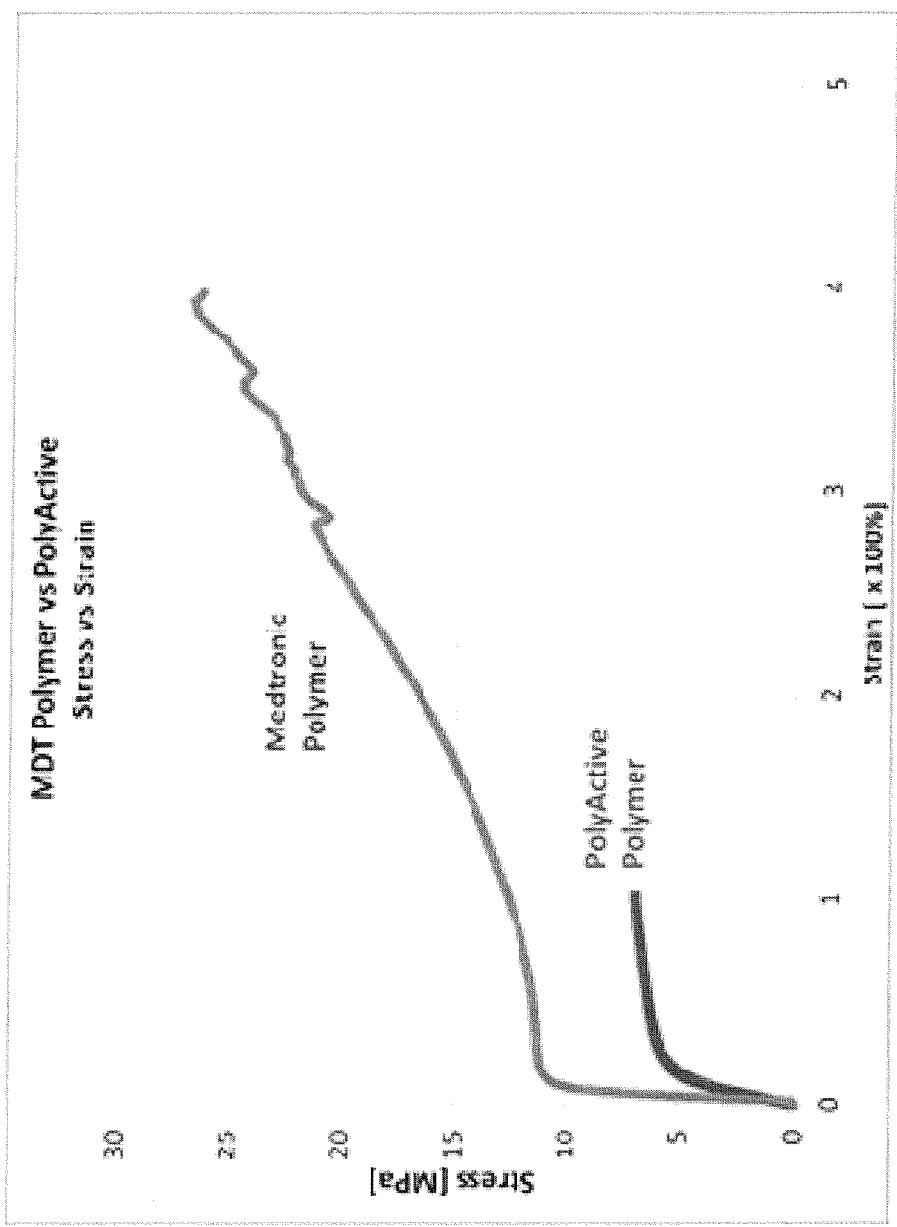
FIG. 2 is a graph comparing the tensile strength (stress vs strain) of a non-biodegradable polymer embodiment of the invention and PolyActive® polymer ("PA").
Figure 3A:
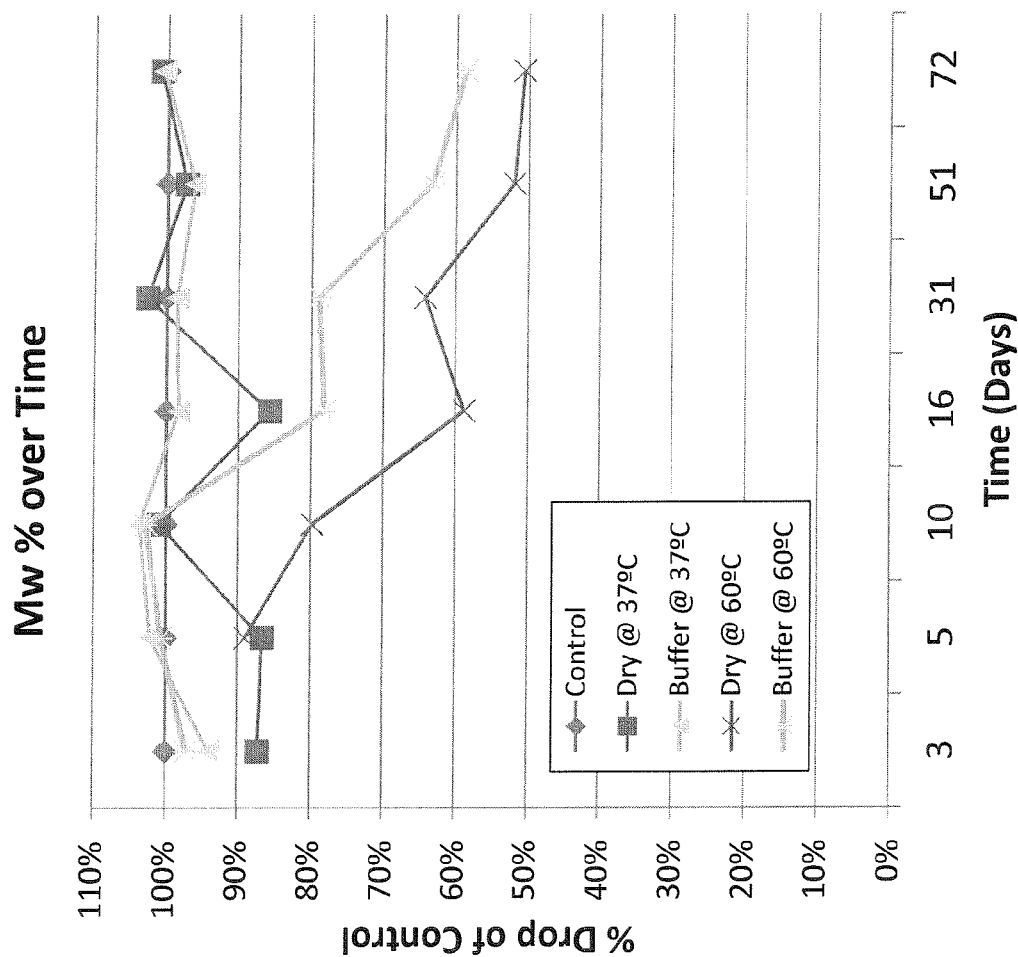
FIGS. 3A and 3B show Mw(thermal) and Mw(hydrolytic) properties of non-biodegradable polymer embodiments of the invention. Films of polymer were made and placed into subsequent test conditions indicated on chart. Films were sampled on indicated time points and analyzed—up to 72 days. Polymer is stable for up to 72 days at body temperature, 37° C. both in dry and wet conditions. This proves the polymer withstands hydrolytic cleavage of the linkages. Polymer experiences thermal degradation, at 60° C., maintaining ~50% of Mw over 72 days.
Figure 3B:
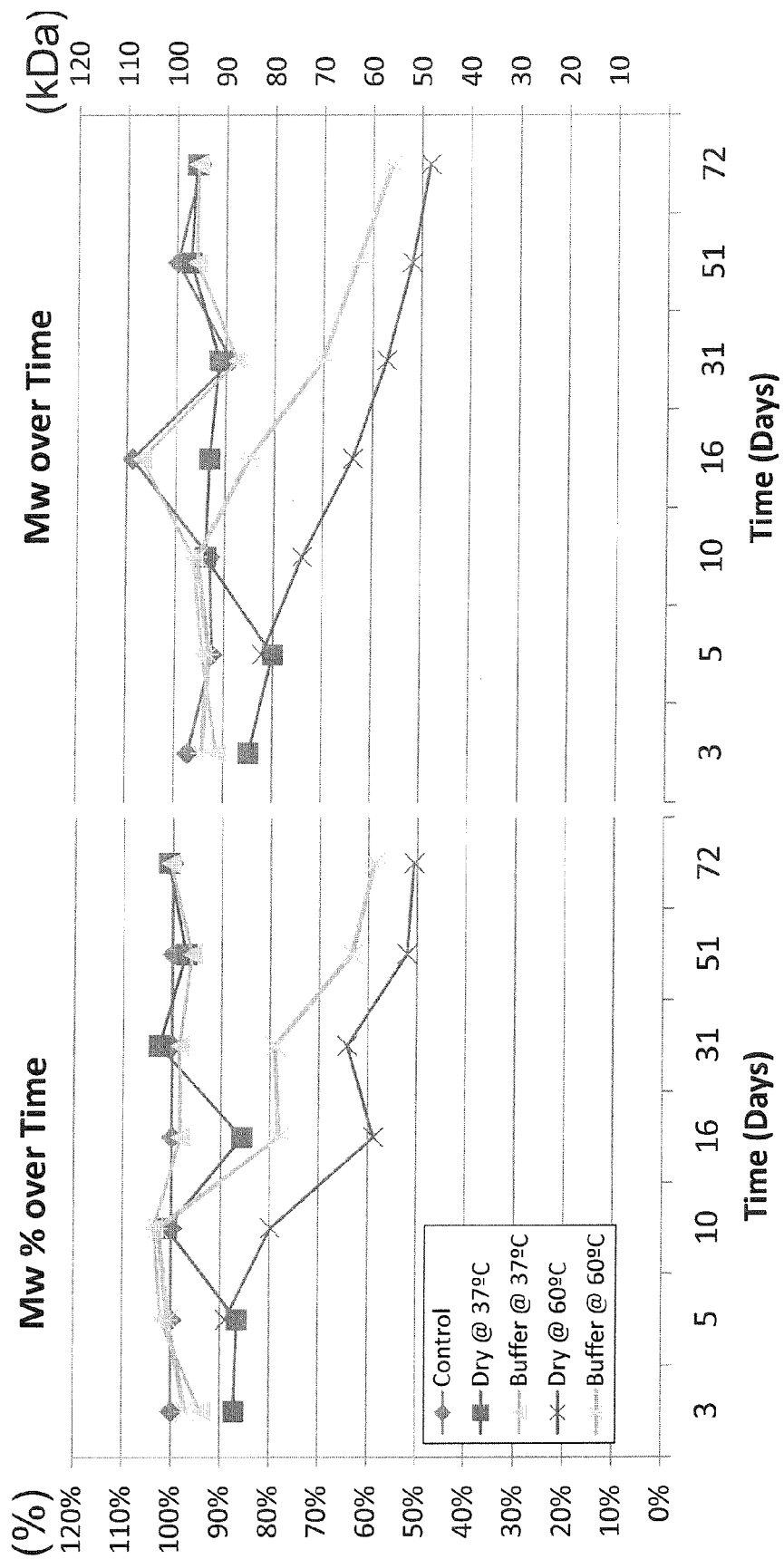
Figure 4:
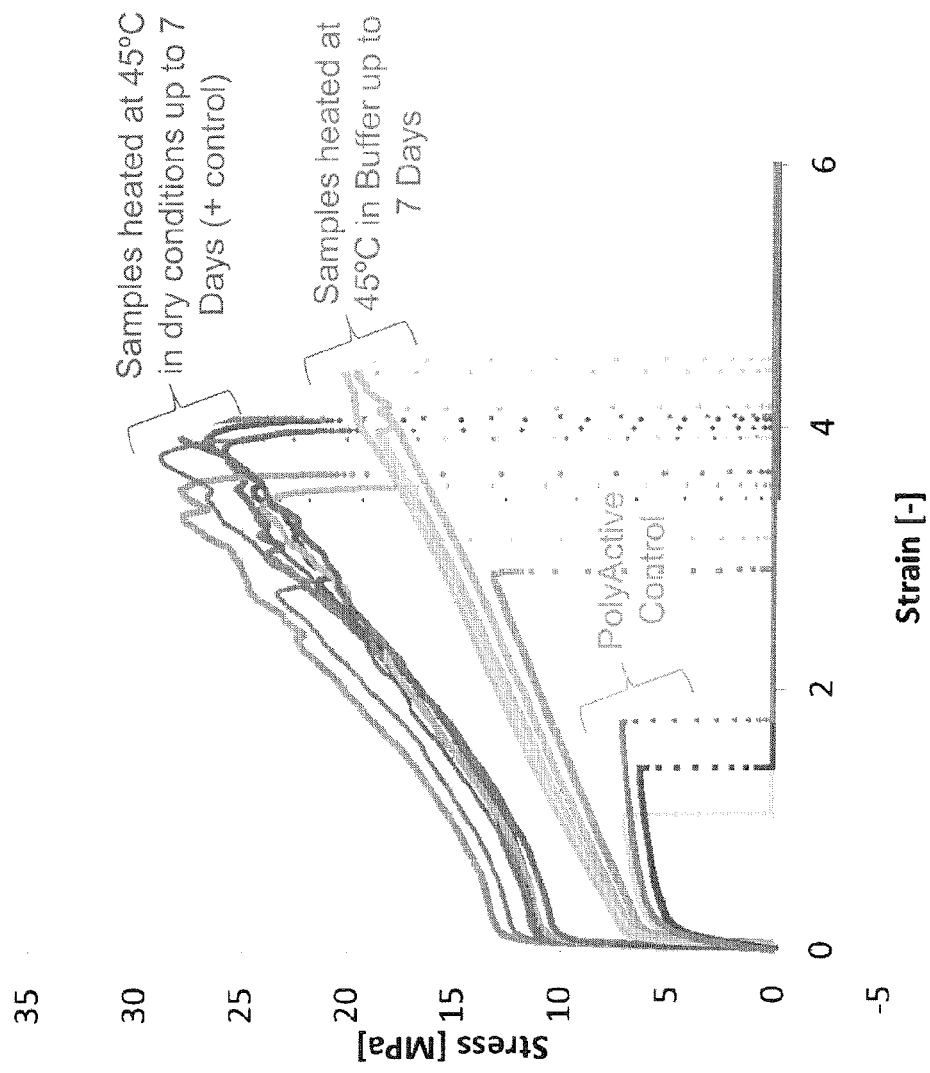
FIG. 4 shows stress strain curves of a non-biodegradable polymer embodiment of the invention. As a general trend, our polymer films heated at 45° C. for the various durations (1 day, 5 days, and 7 days) has roughly the same tensile strength when compared to the control films (7 days—stored in room temperature).

In illustrative embodiments of the invention, the sensor comprises a cylindrical/tubular architecture and has a diameter of less than 1 mm, 0.9 mm, 0.8 mm, 0.7 mm, 0.6 mm, 0.5 mm, 0.4 mm, 0.3 mm or 0.2 mm. In certain examples, the sensor has a diameter of about 0.5 mm or about 0.25 mm. In some embodiments, the body of sensor is formed from a polymeric material. Optionally, the sensor is in the form of a fiber. In some embodiments of the invention, the internal matrix of a cylindrical sensor comprises one or more cavities or voids, for example a encapsulated longitudinal reservoir or cavity. Typically a sensing complex is disposed within such a encapsulated longitudinal reservoir or cavity. In certain embodiments of the invention, the sensor is designed to have certain stress/strain parameters (see, e.g. the stress/strain parameters of the embodiments shown in FIGS. 2 and 4).

Optionally the sensing complex produces an optical signal that can be correlated with an analyte of interest, for example, glucose. A sensing complex (e.g. one comprising a binding assay) generating the optical signal should typically be reversible such that a continuous monitoring of fluctuating levels of analyte can be achieved. Optionally, the detectable or measurable optical signal is generated using a proximity based signal generating/modulating moiety pair so that a signal is generated or modulated when a first member of the pair is brought into close proximity with a second member of the pair. In one illustrative embodiment, the analyte binding agent (e.g. a lectin such as mannose binding lectin as disclosed in WO 2006/061207) is labelled with one of a proximity based signal generating/modulating moiety pair and the analyte analogue is labelled with the other of the proximity based signal generating/modulating moiety pair, and there is a detectable difference in signal when the analyte analogue and analyte binding agent form the complex and when the analyte analogue is displaced by the analyte from the complex. Typically, the proximity based signal generating/modulating moiety pair is an energy donor moiety and energy acceptor moiety pair. Energy donor moieties and energy acceptor moieties are also referred to as donor and acceptor chromophores (or light absorbing materials) respectively. An energy acceptor which does not emit fluorescence is referred to as a quenching moiety. In such embodiments, a lectin can be labelled with one of an energy donor and energy acceptor moiety pair and the analyte analogue is labelled with the other of the energy donor and energy acceptor moiety pair. The detectable difference in signal corresponds to a detectable difference in energy transfer from the energy donor moiety to the energy acceptor moiety. Optionally, the analyte analogue bears the energy acceptor moiety and the analyte binding agent bears the energy donor moiety. In certain embodiments of the invention, the sensor of the invention incorporates an assay which generates an optical readout using the technique of fluorescence resonance energy transfer (FRET).

In one illustrative embodiment of the sensors discussed in the paragraph above, the variants of the competitive binding assay each comprise: an analyte binding agent labelled with a first light-absorbing material; a macromolecule labelled with a second light-absorbing material and comprising at least one analyte analogue moiety; wherein the analyte binding agent binds at least one analyte analogue moiety of the macromolecule to form a complex from which said macromolecule is displaceable by said analyte, and wherein said complex is able to absorb light energy and said absorbed light energy is able to be non-radiatively transferred between one of the light-absorbing materials and the other of the light-absorbing materials with a consequent measurable change in a fluorescence property of said light absorbing materials when present in said complex as compared to their said fluorescence property when said macromolecule is displaced by said analyte from said complex, and wherein the different variants of the assay are distinguished by the number of analyte analogue moieties present in the macromolecule. Such sensors are disclosed, for example in U.S. Patent Application Publication Nos. 20080188723, 20090221891, 20090187084 and 20090131773, the contents of each of which are incorporated herein by reference.

In illustrative embodiments of the invention, sensor elements (e.g. a sensor body, a sensor cap, a sensor membrane or the like) formed from biostable glucose permeable polymer can be bonded to other polymeric elements such as a cap, a membrane, a Polymer Optical Fiber (POF) or the like, with or without use of additional materials (e.g. adhesive compositions). For example, in certain embodiments of the invention, instead of using adhesive for bonding to the fiber, a solvent makes an element such as a membrane/cap and the fiber materials mix/bond at their interface. In this way, without the extra adhesive material, a sensor becomes smaller, faster, more reliable, more reproducible and cheaper. Moreover, the lack of adhesive can eliminate problems where analytes such as glucose have to diffuse though a bonding site (i.e. because considerations such as the permeability of an adhesive composition to the analyte are not an issue).

Typically in such bonding processes, prior to solvent bonding the membrane is placed in close contact with the optical fiber. At the sensor body/cap/membrane-optical fiber bond zone, solvent diffuses from the outer membrane surface to the interface between membrane and fiber where it makes the materials mix/bond. Because the materials of the membrane and the fiber mix the bond gets stronger than a bond between the membrane and an adhesive. Using adhesive bonding, the adhesive has to fill up a necessary gap between membrane and fiber. Adhesive is filled into the gap from the membrane proximal end. In contrast, using solvent bonding, it is possible to bond caps, membranes and the like to fibers and the like with an outer surface consisting of polyvinylidene difluoride ("PVDF", a teflon like material which keeps the light inside the fiber and protect the acrylic core).

Figure 5A:
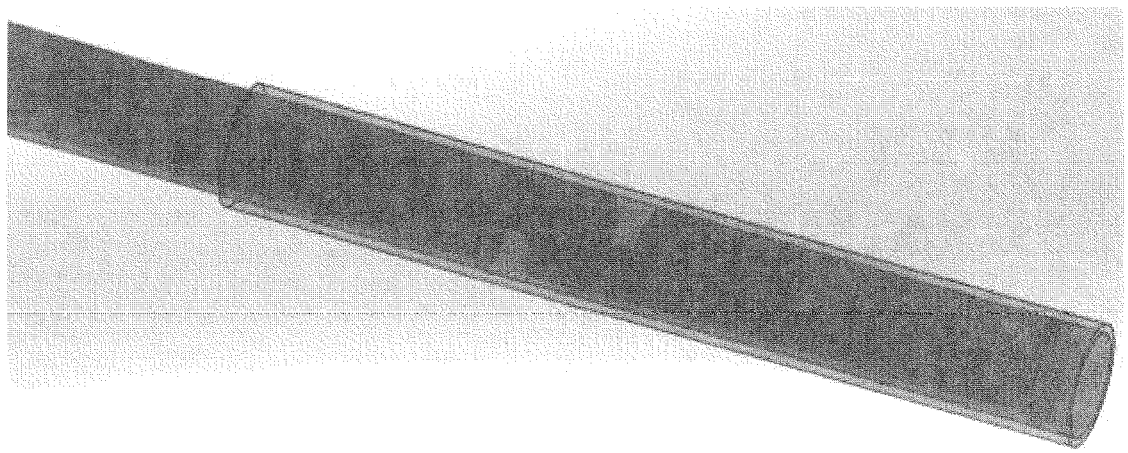
FIGS. 5A and 5B are schematics showing a tubular sensor body formed a non-biodegradable polymer embodiment of the invention. In these schematics, the body is covered by a cap or membrane in a manner that creates internal reservoirs in side of the tubular body (FIG. 5A) or the distal end of the tubular body (FIG. 5B).
Figure 5B:
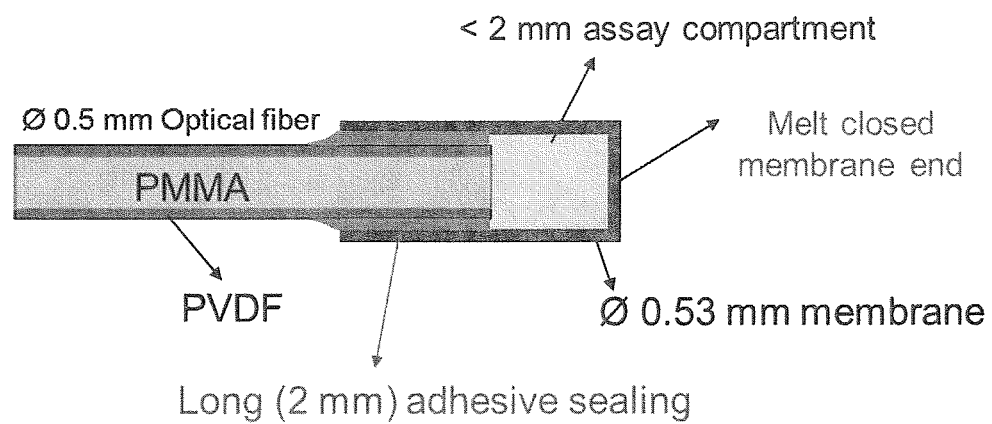
Figure 6:
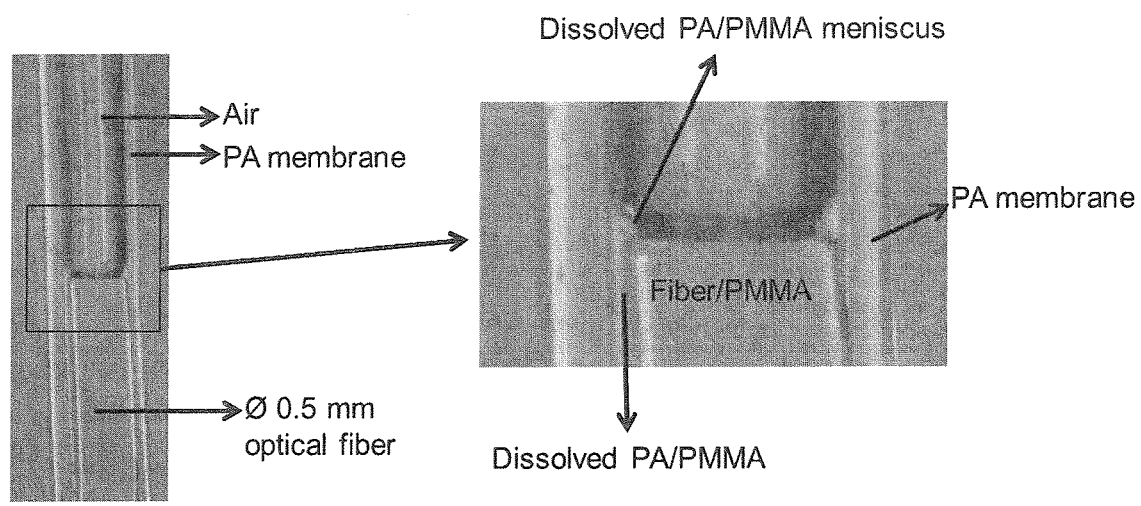
FIG. 6 shows a dibromomethane ("DBM") vapor phase bonded PolyActive™ ("PA") membrane to Poly(methyl methacrylate) ("PMMA") surface.
Figure 7:
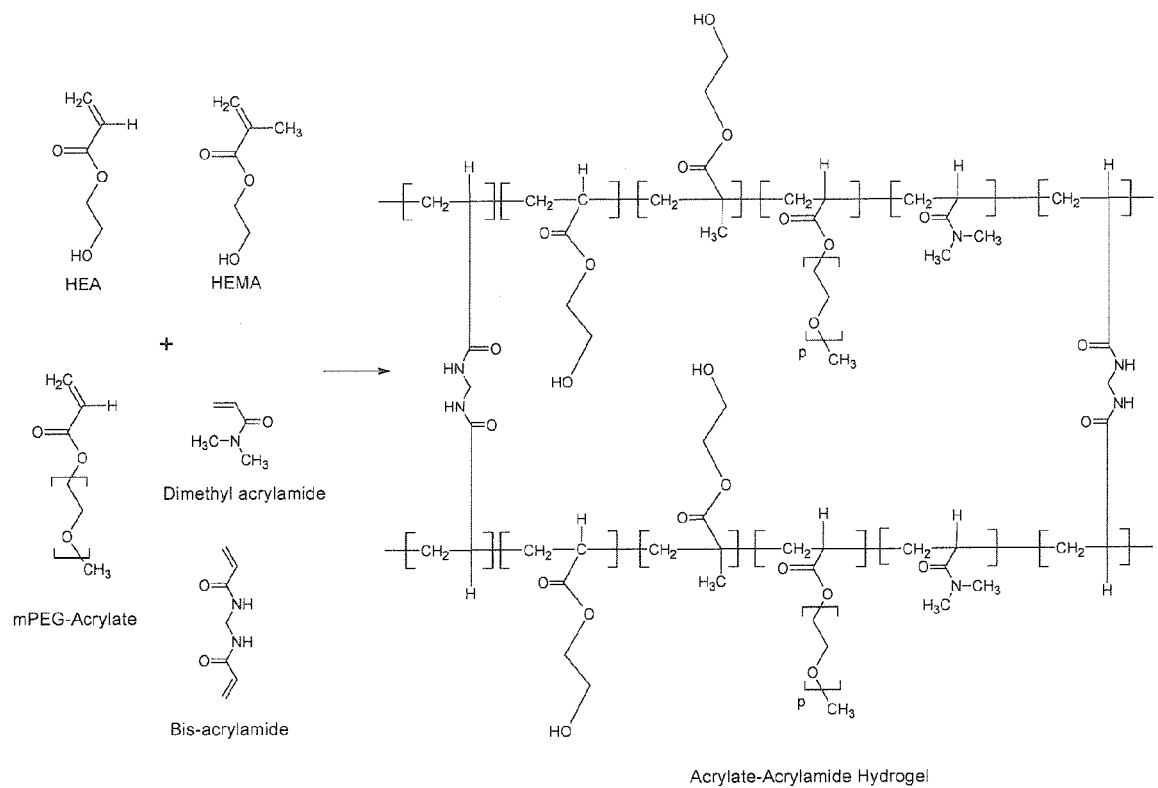
FIG. 7 is a schematic showing a hydrogel for use in embodiments of the invention.

In illustrative embodiments of the invention, the tubular housing comprise an internal reservoir containing a glucose sensing complex comprising at least one glucose binding agent and at least one fluorophore. Typically in these embodiments, the components of the glucose sensing complex are lyophilized. In certain embodiments, the internal reservoir can comprise a hydrogel (see, e.g. FIG. 7). In embodiments of the invention, the tubular housing is between 80 microns and 300 microns in diameter. In some embodiments of the invention, an internal reservoir is disposed on a side of the tubular housing (see, e.g. FIG. 5A). In some embodiments of the invention, an internal reservoir is disposed on a terminal end the tubular housing (see, e.g. FIG. 5B). In illustrative embodiments of the invention, the glucose sensing systems can comprise a processor, wherein the processor performs the steps of assessing optical signal data generated by the glucose sensing complex and transmitted by the optical fiber; and then computing a glucose concentration based upon the optical signal data.

Another embodiment of the invention is method for making a biostable glucose permeable polymer by combining together an isocyanate, a polypropylene glycol-block-polyethylene glycol-block-polypropylene glycol having an average molecular weight ($M_r$) of from about 600 to about 1200 Daltons; and a terephthalate. Optionally the biostable glucose permeable polymers have an average molecular weight of between 10,000 and 1,000,000. Daltons. In this method, the components are combined under conditions which produce a polymeric composition having a glucose permeability of at least $1 \times 10^{-8}$ cm$^2$/s at 37° C. in phosphate buffered saline as well as exhibiting a less than a 5% weight loss after 7 days of implantation in vivo. Typically these methods further comprise using an extrusion process to mold the polymeric composition, for example into a tubular form having a first end and a second end. Typically, the composition is manipulated to for a tubular structure between 80 microns and 300 microns in diameter. Certain methods of the invention include operatively coupling the first end of the tubular housing to an optical fiber so as to form a seal with the first end. These methods can include operatively coupling the second end of the tubular housing to a membrane or a cap so as to form a seal with the second end and an internal reservoir within the tubular housing. Optionally, the methods can comprise disposing a hydrogel in the internal reservoir.

In certain embodiments of the invention, cap or membrane (e.g. one formed from the biostable glucose permeable polymer composition) is coupled to the second end of a tubular housing using a solvent to dissolve the polymeric composition in the cap and/or membrane and the housing material in order to create adhesion between the cap and the second end of the tubular housing (e.g. so that polymers in the polymeric composition and polymers in the optical fiber or polymers in the membrane or cap are entangled and attracted together by Van der Waals forces). In certain embodiments, a cap or membrane is coupled to the tubular housing using a solvent vapor. In embodiments of the invention, the method can comprise disposing a glucose sensing complex within the internal reservoir. Optionally the glucose sensing complex is lyophilized. In embodiments of the invention, the method can comprise disposing a hydrogel within the internal reservoir.

Yet another embodiment of the invention is a hydrophilic polyurea composition formed by combining an isocyanate, a polypropylene glycol-block-polyethylene glycol-block-polypropylene glycol having an average molecular weight ($M_r$) of from about 600 to about 1200 Daltons, and a terephthalate. In this embodiment, the hydrophilic polyurea composition has a glucose permeability of at least $1 \times 10^{-8}$ cm$^2$/s at 37° C. in phosphate buffered saline and is biostable such that the tubular housing has less than a 10% (or 1%) weight loss after 7 days of implantation in vivo. Typically, the hydrophilic polyurea composition comprises polymers have an average molecular weight of between 10,000 and 1,000,000. Daltons.

Embodiments of the invention provide hydrophilic glucose limiting polymeric materials that offer tailored hydration profiles. The superior hydration characteristics of the polymeric materials provide improved biocompatibility and resistance to biofouling. The increased hydrophilicity of the material provides a polymer that can be formed into or coated onto a biosensor without requiring a second coating to enhance surface wetting of the device. In addition, the invention offers polymeric materials whose overall polymeric structure can be controlled by use of a diamine or diol chain extender instead of water. The invention additionally provides polymer blends that offer advantageous features over individual polymeric materials that can be selected in accordance with desired characteristics, for example, long term biostability. Also provided are biosensors having a biocompatible membrane formed from the polymeric compositions of the invention adhered thereto, and methods of measuring an analyte in a tissue of a subject using such a biosensor.

Three characteristics of the biocompatible membranes of the invention that are of particular interest are glucose permeability and biostability. A typical polymeric composition has a permeability constant for glucose mass transport through the material that approximates $1.0 \times 10^{-8}$ cm$^2$/s at 37° C. in phosphate buffered saline. In one aspect, the present invention provides a biocompatible elements formed from a hydrophilic polyurea composition. The hydrophilic polyurea composition comprises the product of a reaction mixture comprising (a) an amino terminated polysiloxane, (b) a hydrophilic polymer selected from the group consisting of a diamino terminated copolymer of polypropylene glycol and polyethylene glycol, polyethylene glycol, polypropylene glycol and diamino polyethylene glycol having an average molecular weight of from about 400 to about 2000, and (c) a diisocyanate selected from the group consisting of hexamethylene-1,6-diisocyanate, dicyclohexylmethane 4,4'-diisocyanate, and isophorone diisocyanate, and constituting about 50 mole % of the reaction mixture. In this mixture, (a) and (b) constitute a polymeric portion of the reaction mixture, and the hydrophilic polyurea composition has a ratio of its diffusion coefficient for oxygen to its diffusion coefficient for glucose of from greater than 2,000 to about 10,000. In one embodiment, the hydrophilic polyurea composition has a ratio of its diffusion coefficient for oxygen to its diffusion coefficient for glucose of from about 3,000 to about 7,000. In an illustrative embodiment, the hydrophilic polyurea composition has a ratio of its diffusion coefficient for oxygen to its diffusion coefficient for glucose of from about 5,000 to about 7,000. As shown in the tables below, the components of the composition and their amounts can be modulated to tune analyte permeability. For example, the biocompatible membrane of the invention can be the product of a mixture having a glucose diffusion coefficient of from about $1\times10^{-9}$ cm$^2$/s to about $200\times10^{-9}$ cm$^2$/s at 37° C., or, from about $2.5\times10^{-9}$ cm$^2$/s to about $10\times10^{-9}$ cm$^2$/s at 37° C.

The biocompatible membrane of the invention can comprise a combination of hydrophobic (polysiloxane) and hydrophilic polymers. In one embodiment, the hydrophilic polymer comprises polyurea (see, e.g., U.S. Pat. Nos. 5,777,060 and 5,786,439, both of which are incorporated herein by reference) and, optionally, polyurethane as well. The membrane includes a blend of two or more polymers, each of which can comprise a combination of two or more polymers with different characteristics, including combinations of hydrophobic and hydrophilic polymers, yielding a solid mixture or blend with desired glucose limiting and performance properties.

In one embodiment, the hydrophilic polymer comprises a diamino terminated copolymer of polypropylene glycol and polyethylene glycol. An illustrative diamino terminated copolymer of polypropylene glycol and polyethylene glycol, comprises poly(propylene glycol)-block-poly(ethylene glycol) bis(2-aminopropyl ether). Suitable hydrophilic polymers for use in polymer blends of the invention have average molecular weights in the range of from about 400 to about 2000, and include poly(propylene glycol)-block-poly(ethylene glycol) bis(2-aminopropyl ether)s (Jeffamine™; Huntsman Chemical) such as Jeffamine 600 (J600), having an average molecular weight (mw) of 600, and Jeffamine 900 (J900), having an average mw of 900; polyethylene glycols (PEGs), such as PEG having an average mw of 600, 1000 or 2000 (PEG 600, PEG 1000, PEG 2000); polypropylene glycols (PPGs), such as PPG having an average mw of 400; and diamino polyethylene glycol (DAPEG), such as DAPEG 2000, having an average mw of 2000.

In one embodiment, the polysiloxane content is from about 15 mole % to about 75 mole % of the polymeric portion of the mixture, or about 50 mole % of the polymeric portion of the mixture. A typical polysiloxane has a molecular weight of about 500 to about 3,500, with a molecular weight of about 2,500 being desirable. In one embodiment, the hydrophilic polymer comprises a combination of J600 and J900. In another embodiment, the polymeric portion of the mixture comprises about 50 mole % polysiloxane, about 25 mole % hydrophilic polymer having an average molecular weight of about 600, and about 25 mole % hydrophilic polymer having an average molecular weight of about 900. Typically, the hydrophilic polymer comprises a diamino terminated copolymer of polypropylene glycol and polyethylene glycol, such as poly(propylene glycol)-block-poly(ethylene glycol) bis(2-aminopropyl ether) (Jeffamine™). Exemplary polymeric compositions for use in the reaction mixture of the invention and their permeability characteristics are described in Table 1 below (wherein "hp" refers to hydrophilic portion). Additional typical polymer combinations and their influence on sensor characteristics are described in Table 2 below.

As shown in Table 2, glucose permeability is more affected than oxygen permeability by changing the characteristics of the hydrophilic component. In these examples, the hydrophilic component is altered by varying the relative amounts of J600 and J900, the latter of which is more hydrophilic than J600 by virtue of its greater molecular weight. Polymer C is an illustration of how these trends can be used to tailor glucose and oxygen permeabilities. This material has the same fractional amount of polysiloxane (PS) therefore maintaining good oxygen permeation. The hydrophilicity of the polymer has been reduced (relative to a J900-PS polymer) by using equimolar amounts of J900 and J600. Because the hydrophilicity has been decreased without compromising the oxygen permeability of the polymer to a great extent, a material with a superior oxygen/glucose permeability ratio is obtained.

Because the temperature of adipose tissue surrounding a subcutaneous glucose sensor could be expected to range from roughly 30 to 40° C., a polymer whose glucose permeability is unaffected by temperature is desirable. Table 2 details the change in glucose permeability (%) observed when cooling the sensor from 37° C. to 27° C. or warming the sensor to 42° C. from 37° C. Interestingly, glucose permeability drops with increasing temperature, whereas oxygen permeability increases with temperature.

The inverse relationship between glucose permeability and temperature is believed to be the result of the known lower critical solution temperature (LCST) of many water-soluble polyethers such as Jeffamine™ 600 and Jeffamine™ 900. The LCST of aqueous solutions of these polymers is manifested by the fact that these polymers are less soluble in water at higher temperatures. Previous data have shown that glucose permeability improves with increasing membrane hydrophilicity. Therefore, if higher temperatures result in a less hydrated membrane due to the LCST characteristics of the polyether segments of the membrane, glucose permeability would also be lessened at higher temperatures. The data in the tables below suggests materials with smaller fractional polyether compositions are less subject to changes in glucose permeability with changes in temperature. Furthermore, polymers with higher Jeffamine™ 900 content in their hydrophilic portion appear to have glucose permeabilities that are less susceptible to changing temperature.

In certain contexts, a polymer with greater than 50% PS content would be beneficial due to the increased oxygen permeability and its reduced susceptibility to temperature modulated glucose permeability. However, the decreased hydrophilicity should be offset with the addition of more Jeffamine™ 900 than Jeffamine™ 600, as the former promotes glucose permeability better than the latter and appears to be less sensitive to thermal changes.

Polymer D, 75% PS-25% Jeff 900, did not show any glucose permeability ($O_2$ permeability was not measured). This suggests that the PS content is best kept below about 75%. A material comprising 60% PS and 40% Jeff 900 (F) may offer advantageous properties. Additionally, 60% PS-30% Jeff 900-10% Jeff 600 (G) would be an additional attractive alternative. Other alternatives that should yield similar results include polymers incorporating polyethylene glycol (PEG), polypropylene glycol (PPG), amino-terminated PEG or PPG, as well as polymeric blends of the polymers incorporating the above components, block copolymers generated from the above components or blends of the above monomers to yield random copolymeric structures.

In addition to the hydrophilic and hydrophobic polymers described above, the reaction mixture comprises a diisocyanate, which constitutes about 50 mole % of the reaction mixture. Examples of diisocyanates include hexamethylene-1,6-diisocyanate (HMDI), dicyclohexylmethane 4,4'-diisocyanate, and isophorone diisocyanate. In some embodiments, 10% excess HMDI is included in the reaction mixture. In some embodiments, the reaction mixture further comprises a chain extender, such as N-methyl diethanolamine (NMDA), ethylene diamine (EDA) or water ($H_2O$).

Factors useful in selecting a polymeric composition for use in a biocompatible membrane of the invention include hydration rate, diffusion coefficient, and sensor performance and linearity. Typical compositions have an initial hydration rate (mg/min for a 5 minute period) at least equal to 29, a diffusion coefficient at least equal to $0.82 \times 10^{-6}$ mm h, and sensor performance in 100 mg/dL glucose solution of between 20 and 70 nA (more typically between 25 and 30 nA) with membrane thickness' (e.g. as measured by reflectometry from a gold plated glass slide coated under the same conditions as the sensors) that will allow for increasing coating thickness in the case of high readings, and reducing thickness in the case of low readings.

The invention provides a biocompatible composition comprising a hydrophilic polyurea having selected in vivo properties. The hydrophilic polyurea composition typically comprises the product of a reaction mixture comprising (a) an amino terminated polysiloxane, (b) a hydrophilic polymer selected from the group consisting of a diamino terminated copolymer of polypropylene glycol and polyethylene glycol, polyethylene glycol, polypropylene glycol and diamino polyethylene glycol having an average molecular weight of from about 400 to about 2000, and (c) a diisocyanate selected from the group consisting of hexamethylene-1,6-diisocyanate, dicyclohexylmethane 4,4'-diisocyanate, and isophorone diisocyanate, and constituting about 50 mole % of the reaction mixture. In this mixture, (a) and (b) constitute a polymeric portion of the reaction mixture, and when the mixture is reacted with (c), the end product polymer has a ratio of its diffusion coefficient for oxygen to its diffusion coefficient for glucose of from about 2,000 to about 10,000. In a typical embodiment, the hydrophilic polyurea composition has a ratio of its diffusion coefficient for oxygen to its diffusion coefficient for glucose of from about 3,000 to about 7,000. In a more typical embodiment, the hydrophilic polyurea composition has a ratio of its diffusion coefficient for oxygen to its diffusion coefficient for glucose of from about 5,000 to about 7,000.

The biocompatible membrane of the invention can include a hydrophilic polymer that comprises a poly(propylene glycol)-block-poly(ethylene glycol) bis(2-aminopropyl ether). The polysiloxane typically has a molecular weight of about 500 to about 3,500, and most typically, about 2,500. In some embodiments, the reaction mixture further comprises a chain extender, such as N-methyl diethanolamine, ethylene diamine, butane diol, diethylene glycol, propane diol or water. The biocompatible membrane of the invention can be the product of a mixture having a glucose diffusion coefficient of from about $1 \times 10^{-9}$ cm$^2$/s to about $200 \times 10^{-9}$ cm$^2$/s at 37° C., or typically, from about $2.5 \times 10^{-9}$ cm$^2$/s to about $10 \times 10^{-9}$ cm$^2$/s at 37° C.

In a typical embodiment, the polysiloxane content is from about 15 mole percent to about 75 mole percent of the polymeric portion of the mixture, or more typically, about 50 mole percent of the polymeric portion of the mixture. In one embodiment, the hydrophilic polymer comprises a combination of a diamino terminated copolymer of polypropylene glycol and polyethylene glycol having an average molecular weight of about 600 and a diamino terminated copolymer of polypropylene glycol and polyethylene glycol having an average molecular weight of about 900. In another embodiment, the polymeric portion of the mixture comprises about 50 mole percent polysiloxane, about 25 mole percent hydrophilic polymer having an average molecular weight of about 600, and about 25 mole percent hydrophilic polymer having an average molecular weight of about 900. Typically, the hydrophilic polymer comprises a diamino terminated copolymer of polypropylene glycol and polyethylene glycol. A typical diamino terminated copolymer of polypropylene glycol and polyethylene glycol is poly(propylene glycol)-block-poly(ethylene glycol) bis(2-aminopropyl ether).

The invention additionally provides methods of measuring an analyte in a tissue of a subject using a sensor having elements formed from the biostable polymer compositions disclosed herein. The method comprises introducing an implantable biosensor of the invention into the tissue of the subject, and detecting the signal generated by the transducer. The amount of signal corresponds to the amount of analyte. Typically, the analyte is glucose although a variety of other analyte sensor systems can be adapted for use with the materials and elements disclosed herein.

The above description is illustrative and not restrictive. Many variations of the invention will become apparent to those of skill in the art upon review of this disclosure. Merely by way of example a variety of solvents, membrane formation methods, and other materials may be used without departing from the scope of the invention. The scope of the invention should, therefore, be determined not with reference to the above description, but instead should be determined with reference to the appended claims along with their full scope of equivalents. All publications, patents and patent applications mentioned in this specification are herein incorporated by reference into the specification to the same extent as if each individual publication, patent or patent application was specifically and individually indicated to be incorporated herein by reference.

EXAMPLES

Example 1: Illustrative Synthesis Procedure for Biostable Polymer Embodiments

Illustrative Materials and Tools for Synthesis of Polymer Embodiments

Tetrahydrofuran, anhydrous, inhibitor free (THF).
Jeffamine900.
Bis(2-hydroxyethyl) terephthalate.
4,4'-Methylenebis (cyclohexyl isocyanate) (HMDI).
Di-n-butyltin bis(2-ethylhexanoate) (Tin catalyst).
De-ionized or processed water.
Nitrogen Gas.
Jacketed resin kettle/flask with inlet/outlet adapters—chose appropriate size with polymer batch.
Overhead mechanical stirrer.
Laboratory Balance.

Syringe pump Circulation water bath with temperature control.
Vacuum Oven.
Disposable polypropylene luer-lock syringes—chose appropriate sizes with polymer batch size.
Stainless steel syringe needles—chose appropriate sizes with polymer batch size.
4.0 liter glass beakers
4.0 liter industrial laboratory blender
Molecular wire sieve, #50 mesh Illustrative Steps for Synthesis of Polymer Embodiment The following synthesis procedure describes the formulation of 600 grams of Polyurethane:
Terephthalate (PUT) Polymer. This reaction can be scaled up and scaled down accordingly.
Set Up of Polymer Synthesis:
Hot Air or Oven-Dry the Following:
 3.5 L jacketed resin reaction flask with 4-neck, 24/40 joint reaction head. Viton O-ring.
 Stirring rod and stirrer bearing adapter for mechanical overhead stirrer.
Equipment Setup
 Insert stirring rod with paddle blade into the jacketed reaction flask.
 Put the Viton O-ring in place on top of the reaction flask.
 Place the 3-neck reaction flask head on top of the Viton O-ring and secure with the clamp.
 Seal the openings of the flask head with the 24/40 rubber septa.
 Introduce the nitrogen purge line via a needle into one of the 24/40 septa. There should be constant nitrogen flow, blanketing the entire reaction vessel.
 Connect the jacketed inlet/outlet adapters to a circulating water bath.
 Set the circulating water bath temperature to 40° C.
 Place the syringe pump on an adjustable stand, and raise to level above the reaction head flasks. (A syringe with HMDI will be dosing into the reaction head via a Teflon cannula at a later step).
Addition of Reactants
Bis(2-hydroxyethyl) terephthalate
 Weigh out 139.50±0.20 grams into a tared beaker.
 Record actual weight.
 Quantitatively transfer to the reaction flask.
 Rinse with 400 mL of THF into the reaction flask.
JeffAmine900
 Weigh out 238.44±0.20 grams into a tared beaker.
 Record actual weight.
 Quantitatively transfer to the reaction flask.
 Rinse with 400 mL of THF into the reaction flask.
 Turn on the mechanical stirrer and begin mixing the reaction mix.
 Allow the mixture to completely dissolve.
Di-n-butyltin bis(2-ethylhexanoate) (Tin catalyst)
 Weigh out 1600±15 milligrams into an addition funnel.
 Record actual weight.
 Quantitatively transfer to the reaction flask.
 Rinse with 400 mL of THF into the reaction flask.
Methylene Bis(Cyclohexyl Isocyanate) (HMDI)
 Into a preweighed syringe, measure out 222.12±0.20 grams.
 Record actual weight.
 Place the syringe in the syringe pump and affix the luer lock Teflon cannula onto the syringe. Place the dispensing end of the cannula into one of the 24/40 rubber septa on the reaction head. Lower the delivery end of the cannula so that the HMDI will dose directly into the reaction mix.
 Set the dosing rate to deliver the entire quantity over 25 minutes.
 Rinse the syringe with 400 mL of THF into the reaction flask.
Polymerization
 Increase the circulating water bath temperature to 60° C.
 Allow the reaction to proceed for 22-24 hours, held at 60° C.
 Add 80 mL of D.I. or processed water to the reaction, maintaining stirring and heating for an additional 3-4 hours.
Work up and isolation of polymer.
 Turn off the circulating water bath and disconnect the lines from the reaction flask. Allow the reaction solution to cool to room temperature for 20 minutes.
 Fill the 4.0 L industrial blender with 3.0 L of D.I. or process water.
 Pour in roughly 600 mL of the reaction solution in to the blender and secure the lid.
 Turn on the blender at the low setting of 15,000 rpm for 10 seconds.
 Pour the blended polymer solution through a mesh sieve.
 Collect the polymer. Discard the water in appropriate hazardous waste.
 Repeat steps for the remaining of the reaction mixture in the reaction flask.
 Fill a 4.0 L glass beaker with 3.0 L of D.I. or process water.
 Separately boil water in a 4.0 L glass beaker using a hot plate.
 Take the collected polymer and place in the boiling water for 10 seconds. Quickly remove and place the boiled polymer into a cool water beaker.
 Repeat steps for the remaining of the collected polymer from step. The polymer is patted dry and collected into a large crystallization dish.
 Dry the polymer in a vacuum oven at 25-35" Hg at 45±2° C. for 12-18 hours. Remove polymer from vacuum oven and allow to cool to room temperature.
 Weigh the polymer and record its weight.
 Place into appropriate sized properly labeled container.
Storage
 The polymer can be stored in an amber glass jar in the freezer at −10° C.
Disposal
 The polymer contains no hazardous material and can be discarded in the regular laboratory trash.
Typical Parameters of Polymers Formed by these Methods
 Typical polymer Molecular Weight: 100-200 kDaltons.
 Typical polymer Glucose Permeability: Above $5.0 \times 10^{-8}$ $cm^2$/sec.

Example 2: Illustrative Methods for Coupling Sensor Bodies to Caps, Optical Fibers and the Like The sensor body made from the polymer described in the Example above is typically joined with other elements. One way to couple/affix additional elements such as a membrane, a cap and or an optical fiber to a sensor body includes the use of adhesive compositions. Using the framework of Hansen Solubility Parameters (HSP) and Relative Energy Differences (RED) between adhesive and polymer (PA, PVDF) it can be found that epoxies are suitable adhesives to use. Alternative adhesives include, for instance UV curable acrylates, cyanoacrylates etc.

As discussed in details below, alternatively, such adhesives can be replaced by dissolution bonding e.g. by using a solvent such as dibromomethane (DBM), which is a solvent useful to produce the PA membrane by dipping. Thus, it has been found that DBM dissolves both PA and the optical fiber core material PMMA. With solvent at the interface the materials mix and in this way the bonding mechanism is molecular entanglement and cohesion.

The solvent can be applied in different ways which can, for example, rely on using a membrane with intimate contact (ID<0.5 mm) with the PMMA optical fiber core material.

Illustrative techniques are briefly summarized discussed below.

Solvent Dispensing

The solvent is dispensed directly on the PA membrane with PMMA fiber core underneath. This may take several drops depending on the solvent vapor pressure. The solvent reaches the PA/PMMA interface by diffusion.

Exposure to Saturated Solvent Vapor

A saturated vapor (Relative Humidity RH=100%) is in equilibrium with its corresponding liquid. Therefore, exposure to the saturated vapor is exactly the same as exposure to the liquid.

Illustrative Saturated DBM Vapor Phase Gluing Procedure

Below are illustrative vapor phase gluing procedure steps are listed.
1) 50 mm long optical fibers (Ø0.5 mm) and membranes (fabricated by dipping) are prepared as usual (cut, polished, cleaned).
2) PVDF is removed with e.g. ethyl acetate by dipping the fiber tip. The amount of ethyl acetate in a beaker is adjusted so that approx. 1-2 mm of the PVDF is treated when touching the bottom of the beaker with the fiber. The fiber is dipped in and out of the liquid for about 30 s (approx equal time of 15 s in the liquid and outside). It is important that the tip is clean from PVDF. Inspect in a microscope. The border between covered and uncovered PMMA is easily seen.
3) The tip is dried with a lint-free cloth. Some force (squeezing between the fingers or nails) may be used to pull off all of the softened PVDF. Ensure no dust etc. from cloth on the fiber by inspection in a microscope.
4) The 00.5 mm membranes are put into DI water to expand the opening so that they are easily slid onto the fiber. It is important to use membranes with smaller inner diameter (dry state) than the fiber diameter to ensure intimate contact with the optical fiber.
5) The membranes are put onto the fiber so that at least 1-2 mm is over the PVDF. This is to ensure that no dissolved PMMA is allowed to run out downwards during vapor phase gluing.
6) The fibers with membranes are placed in the exicator 45 mins. It is attractive to get a small PMMA meniscus at the fiber front edge.
7) After gluing wait at least the same time as used for the gluing before filling the membrane. This is to allow diffused DBM to escape again so that it is not interfering with the assay chemistry. At best wait till the next day to be certain until we know more about how DBM might attack the assay.

Illustrative Process for Membrane End Closing

It has also been found that PA dissolved in DBM can in general be used to close/repair PA membranes after e.g. assay filling. Highly concentrated solutions (5-10 Wt % PA in DBM) have been found good when closing Ø0.5 mm ID PA membranes. The high concentration/viscosity ensures that sufficiently large drops can be picked up with a metal pin, e.g. a syringe needle. Drops with diameter larger than the membrane ID are necessary to ensure complete closing with the first drop placed at the end of the membrane. Large drops also makes it easier to reach picking up the next drop before DBM in the first has evaporated. During the DBM evaporation new drops may be placed. Usually 3 to 10 drops are adequate. It is easiest to close a membrane which is already somehow closed in the other end because then the entrapped air in the tube counteract the capillary force on liquid PA and thus stops it from entering the inside membrane. It should be mentioned that if the surface of the drop on the membrane gets concave air may be entrapped when the next drop is placed, which is usually unwanted for reliability reasons.

These membrane closings have proved just as reliable as melt closings, but have a number of very important advantages.

Structuring of the POF by Dissolution

Solvents may be used to structurally design the POF sensors. This can e.g. be done by selective dissolution. One possible design could be made by the following procedure on the PVDF-PMMA POF:

Over a distance of say 2 mm from the fiber tip the PVDF cladding is perforated with e.g. a laser. Several holes are made.

The tip is dipped a little more than 2 mm into e.g. DBM which selectively dissolves the PMMA. We now have a POF with a 2 mm end which consist of a hollow perforated PVDF tube.

At a distance of about 4 mm from the fiber end a ring PVDF around the fiber is removed with e.g. DMF or acrylamide.

The hollow PVDF tube is completely filled with assay.

Right after assay filling the fiber tip is overcoated with dissolved PA to a distance of about 5 mm from the end of the fiber. The PA will only dissolve glue to the exposed PMMA from step 3. Besides, the assay is kept inside the membrane/PVDF tube by the super-hydrophobic interface between the two materials.

In this way a POF integrated assay compartment which structurally supports/strengthen the membrane is created.

Illustrative DMSO Vapor Phase Bonding Equipment

Dry N2 inlet flow.

Tube with DMSO/N2.

Excess DMSO outside bond zone sucked away.

One challenge of using DMSO vapor for PUT01 membrane bonding to optical fibers is to only dissolve the PUT01 and the PVDF in the region where the bond is needed.

It is possible to make the bond by blowing saturated DMSO vapor at 65° C. directly onto the bond region.

Drechsel bottle.

Flat chamber with through hole. Only bond zone is placed inside chamber.

Fixture for optical fiber with membrane.

The equipment consists of a little chamber held by optical tools/fixtures. The optical fiber with the membrane to be bonded is placed in a hole through this chamber such that only the bond region is inside the chamber. When vapor is led to the chamber it flows out to the ambient at the PUT01/fiber bond region. To further limit attack of DMSO outside the bond region vapor is also sucked away close to the membrane. Vapor flow is established by blowing dry (DMSO is hygroscopic!!) N2 through a Drechsel bottle containing DMSO. All parts are placed inside an oven at 65° C.

A first bond can be made using an extruded ID 250 µm membrane, 65° C., 5 min exposure and unspecified DMSO flow Clearly, DMSO flow, vapor removal, time had to be adjusted to limit the dissolution speed. The bond between the PUT01 material and the fiber was tested in wet condition: A strong bond between PUT01 and the fiber was achieved i.e. it was impossible to pull of the PUT01 material from the fiber.

Flat chamber with through hole. Only bond zone is placed inside chamber.

Hole in chamber.

Tube leading DMSO/N2.

A better control of DMSO vapor flow can be introduced by inserting a needle valve on the supply of the N2 carrier gas. Also, two small stainless steel tubes to suck away excess DMSO outside the bond region have been mounted on the bond equipment.

Needle valve for better control of the N2 carrier gas/DMSO vapor flow to the bond region.

Steel tubes to suck/blow air/DMSO away from regions outside the bonding region.

Using this equipment improvements one new membrane—fiber bonding has been made. The membrane was of the extruded ID 250 μm type. This time with the needle valve the DMSO flow could (and was) be adjusted to a much lower level.

The vapor phase equipment can be equipped with two flow-meters. One is for the DMSO carrier N2 gas, the other is for the N2 gas to blow excess DMSO outside the bond region away. For this, only one N2 supply is used. The measurement ranges for the flow meters are 0.1-1.2 LPM and 1-10 LPM respectively. Just looking at the amount of bubbles in the DMSO with a N2 carrier gas flow rate of 0.1 LPM, it was considered to be possible to make good bonds with the use of these flow meters.

The first vapor phase bonded fiber/membranes have been made using membranes made by ourselves (ID 240 μm) and where vapor/gas flow is monitored.

PUT01 is dissolved at the interfaces to the fiber.

One improvement is that we can get a more stable temperature at 65° C. in the bond region by having long (or high volume) N2 gas tubes in the oven.

Illustrative Process for DMSO Vapor Phase Bonding Equipment

Bonding of membranes to fibers have been very successful using DMSO vapor.

Common settings in experiments are:

1) Before bonding, the equipment with new fiber/membrane mounted and perhaps fresh DMSO is allowed to equilibrate at 65° C. for 1-2 hrs.

2) DMSO N2 carrier gas flow is 0.1 L/min.

3) N2 flow of 2 L/min to blow away excess DMSO vapor.

Following such processes, the following is noted:

1) Compared to the use of liquid DMSO for bonding the membrane shape in bond region is almost not changed in this process.

2) The membrane is almost unaffected beyond the fiber distal end and this is also the case for the fiber beyond the membrane proximal end. This means that the N2 blow away of excess DMSO vapor works well.

3) Both 5 min and 10 min treatment results in strong bonds. The 10 min treatment gives a bond which is so strong that the membrane cannot be pulled off (with the hands using tweezers). Instead the membrane material breaks.

4) In both cases there is room for improvement concerning bonding all the way to the fiber distal end.

5) When pulling the membrane in the 10 min exposure case the zone where bond failure (really rupture of the PUT01/PVDF interphase) has occurred can be seen as thinning of the membrane thickness.

It has been shown that heat (e.g. 65° C.) in our liquid DMSO solvent bonding process can be replaced by UV light irradiation. This can provide simpler and reduced processing and it could probably also be implemented in vapor phase DMSO solvent bonding.

TABLES

TABLE 1

| Designation | Composition | Hydration Initial Rate (mg/min) | Hydration % Max | Diffusion Coefficient (mm*h) × 10e⁻⁶ | Intrinsic Viscosity (mL/g) | nA @100 mg/dL | Signal Min-Max (nA) | $R^2$ | Thickness (μm) |
|---|---|---|---|---|---|---|---|---|---|
| | 75/25 J600/PS510 | 29 | 37 | 0.82 | 30 | 25-39 | 22-62 | 0.997-0.999 | 2.7 |
| 936-53 | 85/15 J600/PS510 | 52.5 | 46 | 1.64 | 20 | 70.1 | 59-105 | 0.998 | 1.6 |
| 936-11 | hp-75/25 J600/P600 | 23 | 32 | 0.59 | 35 | 39.2 | 35.5-42.4 | 1 | 3.8 |
| 936-15 | hp-100 J900 | 97 | 54 | 15.5 | 50 | 195.8 | 149-236 | 0.974 | 2.3 |
| 936-22 | hp-75/25 J600/J900 | 28.5 | 43 | 2.76 | 38 | 64 | 60.7-71.5 | 0.999 | 3.6 |
| 936-42 | hp-90/10 J600/J900 | 68.5 | 35 | 1.7 | 21 | 42.8 | 39.1-47.1 | 0.998 | 2.8 |
| 985-67 | hp-85/15 J600/J900 | 58 | 42 | 1.67 | 26 | 68.6 | 65-72 | 0.999 | 2.2 |
| 985-23 | 35/20/45 J600/J900/PS510 | 11 | 5 | 0.24 | 46 | 23.6 | 23.3-24.1 | 1 | 2.6 |
| 985-79 | 75/25 J600/PS510 w/EDA Extension | 51.5 | 38 | 1.33 | 16 | 49.2 | 43.5-56.6 | 0.997 | 1.9 |
| | 2% Blend of 75/25 J600/PS510 w/ hp-100 J900 | 49 | 30 | 1.09 | N/A | 36.1 | 29.9-46.1 | 0.999 | 2.5 |

TABLE 1-continued

|  |  |  |  |  |  |  |  |  |  |
|---|---|---|---|---|---|---|---|---|---|
|  | 5% Blend | 56.5 | 31.6 | 1.56 | N/A | 54.2 | 42.3-76.6 | 0.999 | 2.1 |
|  | 11% Blend | 62 | 31.9 | 1.32 | N/A | 49 | 44-55 | 0.998 | 2.2 |
|  | 15% Blend | 60 | 37.3 | 1.52 | N/A | 58.8 | 54-62 | 0.998 | 2.3 |
|  | 20% Blend | 65 | 36.7 | 1.92 | N/A | 57.6 | 32.4-69.9 | 0.993 | 2.3 |
| 1001-39 | 50/50 DAPEG2000/ PS510 | 280.9 | 52 | 38.4 | 36 |  |  |  |  |
|  | 2% Blend of 75/25 J600/PS510 w/1/1 DAPEG2000/ PS510 | 51 | 28.5 |  |  | 36.3 | 34-40 | 1 | 2.6 |
|  | 5% Blend | 54 | 21.5 |  |  | 43.5 | 41-45 | 0.999 | 2.5 |
|  | 15% Blend | 58 | 11.7 |  |  | 61.9 | 58-67 | 0.999 | 2.5 |
| 927-34(76) | hp:50% peg600 | 15 | 37 | 0.06 | 46 | 12 | 10 to 14 | 0.999 | 1.8 |
| 927-40 | hp:50% peg1000 | 77 | 98 | 9.23 | 39 | 103 | 100 to 108 | 0.997 | un-even |
| 927-43 | hp:50% jeff900 | 60 | 47 | 3.88 | 40 | 136 | 117 to 151 | 0.993 | 1.8 |
| 927-48 | 80% jeff600 | 52 | 39 | 2.32 | 23 | 32 | 28 to 35 | 0.998 | 2.5 |
| 927-52 | hp:25% ppg400 | 24 | 21 | 0.54 | 31 | 26 | 23 to 33 | 0.999 | 1.7 |
|  |  |  |  | 0.47 |  |  |  |  |  |
| 927-54 | hp:50% ppg400 | 10 | 12 | 0.04 | 23 | 6 | 7 to 32 | 0.978 | 4.1 |
| 986-17 | 65% jeff600 | 22 | 20 | 0.22 | 32 | 18 | 17 to 20 | 0.999 | 3.2 |
| 986-49 | nmda/ extension | 38 | 29 | 0.79 | 27 | 24 | 23 to 25 | 0.999 | 2.9 |
| 986-63 | 10% excess hmdi | 42 | 31 | 0.79 | 20 | 26 | 25 to 35 | 0.998 | 3.4 |

| Designation | Composition | Theta (air) | | | Theta (AI) | | |
|---|---|---|---|---|---|---|---|
|  |  | Dry | Hydrated | Post-hydration | Dry | Hydrated | Post-hydration |
| 936-53 | Production Material 85/15 J600/PS510 | 109.1 | 97.9 | 106.8 | 113.1 | 95.3 | 104.2 |
| 936-11 | hp-75/25 J600/P600 | 100.1 | 98.6 | 107.8 | 103.4 | 105.3 | 109.8 |
| 936-15 | hp-100 J900 |  |  |  |  |  |  |
| 936-22 | hp-75/25 J600/J900 |  |  |  |  |  |  |
| 936-42 | hp-90/10 J600/J900 |  |  |  |  |  |  |
| 985-67 | hp-85/15 J600/J900 | 103.9 | 106.2 | 105 | 112 | 109.1 | 108.7 |
| 985-23 | 35/20/45 J600/J900/ PS510 | 93.6 |  |  | 105.4 |  |  |
| 985-79 | Production Ration w/ EDA Extension | 108.1 | 105.9 |  | 111.4 | 106.2 |  |
|  | 2% Blend of Production w/hp- 100 J900 |  |  |  |  |  |  |
|  | 5% Blend |  |  |  |  |  |  |
|  | 11% Blend |  |  |  |  |  |  |
|  | 15% Blend |  |  |  |  |  |  |
|  | 20% Blend | 107.2 | 105.2 |  | 93.8 | 102.7 |  |
| 1001-39 | 50/50 DAPEG2000/ PS510 | 109.1 | 79.3 | 105.4 | 103.5 | 51.2 | 105.4 |

TABLE 2

| Polymer | Membrane Composition Polysiloxane | Jeff 900 | Jeff 600 | Oxygen Permeability ($cm^2/s$) × $10^{-5}$ | Glucose Permeability ($cm^2/s$) × $10^{-9}$ | $O_2$/Glucose Permeability Ratio | Percent Change in Glucose Permeability from 37° C. 27° C. (high) | 42° C. (low) |
|---|---|---|---|---|---|---|---|---|
| A | 50% | 50% | | 2.9 | 27 | 1074 | 18% | −19% |
| B | 50% | | 50% | 2.0 | Below detection limit | N/A | | |
| C | 50% | 25% | 25% | 2.3 | 4.4 | 5227 | 41% | −15% |
| D | 75% | 25% | | 2.2 | Below detection limit | N/A | | |
| E | 25% | | 75% | 1 | 5.0 | 2000 | 64% | −42% |
| F | 60 | 40 | | — | — | — | — | — |
| G | 60 | 30 | 10 | — | — | — | — | — |

What is claimed is:

1. A glucose sensing system comprising:
a tubular housing having a first end and a second end, wherein:
the tubular housing comprises a polymeric composition formed by combining:
an isocyanate;
a polypropylene glycol-block-polyethylene glycol-block-polypropylene glycol having an average molecular weight ($M_r$) of from about 600 to about 1200 Daltons; and
a terephthalate; and
the polymeric composition has a glucose permeability of at least $1 \times 10^{-8}$ $cm^2$/s at 37° C. in phosphate buffered saline.

2. The glucose sensing system of claim 1, wherein the polymeric composition is biostable such that the tubular housing has less than a 5% weight loss after 7 days of implantation in vivo.

3. The glucose sensing system of claim 1, wherein:
(a) the first end of the tubular housing is coupled to an optical fiber so as to form a seal with the first end; and/or
(b) the second end of the tubular housing is coupled to a membrane or a cap, thereby forming an internal reservoir within the tubular housing.

4. The glucose sensing system of claim 3, wherein the tubular housing is coupled to the optical fiber and/or the cap by solvent bonding such that polymers in the polymeric composition and polymers in the optical fiber or polymers in the cap are entangled and attracted together by Van der Waals forces.

5. The glucose sensing system of claim 3, wherein the tubular housing comprises:
(a) an internal reservoir containing a glucose sensing complex comprising at least one glucose binding agent and at least one fluorophore; and
(b) the components of (a) are lyophilized.

6. The glucose sensing system of claim 1, wherein the tubular housing is between 80 microns and 300 microns in diameter.

7. The glucose sensing system of claim 3, wherein the internal reservoir comprises a hydrogel.

8. The glucose sensing system of claim 3, wherein the internal reservoir is disposed on a side of the tubular housing.

9. The glucose sensing system of claim 5, further comprising:
a processor, wherein the processor performs the steps of:
assessing optical signal data generated by the glucose sensing complex and transmitted by the optical fiber; and
computing a glucose concentration based upon the optical signal data.

10. A method for making a glucose sensor comprising the steps of:
(a) combining together an isocyanate, a polypropylene glycol-block-polyethylene glycol-block-polypropylene glycol having an average molecular weight ($M_r$) of from about 600 to about 1200 Daltons; and a terephthalate;
(b) allowing the combination of (a) to form a polymeric composition having a glucose permeability of at least $1 \times 10^{-8}$ $cm^2$/s at 37° C. in phosphate buffered saline;
(c) using an extrusion process to mold the polymeric composition into a tubular housing having a first end and a second end.

11. The method of claim 10, wherein the method comprises operatively coupling the first end of the tubular housing to an optical fiber so as to form a seal with the first end.

12. The method of claim 11, wherein the method comprises operatively coupling the second end of the tubular housing to a membrane or a cap so as to form a seal with the second end and an internal reservoir within the tubular housing.

13. The method of claim 12, further comprising disposing a hydrogel in the internal reservoir.

14. The method of claim 12, wherein the cap is formed from the polymeric composition and is coupled to the second end using a solvent to dissolve the polymeric composition and create adhesion between the cap and the second end of the tubular housing.

15. The method of claim 14, wherein the cap is coupled to the tubular housing using a solvent vapor.

16. The method of claim 10, wherein the method comprises disposing a lyophilized glucose sensing complex within the internal reservoir.

17. The method of claim 10, wherein the tubular housing is between 80 microns and 300 microns in diameter.

18. The method of claim 10, wherein the polymeric composition is formed to exhibit a less than a 10% weight loss after 7 days of implantation in vivo.

19. The method of claim 10, wherein the polymeric composition is formed from polymers having an average molecular weight of between 10,000 and 1,000,000 Daltons.

20. A hydrophilic polyurea composition shaped to form a tubular housing, and formed by combining:
- an isocyanate,
- a polypropylene glycol-block-polyethylene glycol-block-polypropylene glycol having an average molecular weight ($M_r$) of from about 600 to about 1200 Daltons; and
- a terephthalate;

wherein:
- the hydrophilic polyurea composition has a glucose permeability of at least $1\times10^{-8}$ cm$^2$/s at 37° C. in phosphate buffered saline and
- wherein the hydrophilic polyurea polymeric composition is biostable such that the tubular housing has less than a 5% weight loss after 7 days of implantation in vivo.

* * * * *